United States Patent
Chippett

(10) Patent No.: US 7,021,820 B2
(45) Date of Patent: Apr. 4, 2006

(54) LOW THERMAL INERTIA SCANNING ADIABATIC CALORIMETER

(75) Inventor: Simon Chippett, 30 Ginn Rd., Winchester, MA (US) 01890

(73) Assignee: Simon Chippett, Winchester, MA (US)

( * ) Notice: Subject to any disclaimer, the term of this patent is extended or adjusted under 35 U.S.C. 154(b) by 14 days.

(21) Appl. No.: 10/889,093

(22) Filed: Jul. 12, 2004

(65) Prior Publication Data

US 2005/0008063 A1    Jan. 13, 2005

Related U.S. Application Data

(60) Provisional application No. 60/485,949, filed on Jul. 10, 2003.

(51) Int. Cl.
*G01K 17/04* (2006.01)
*G01N 25/20* (2006.01)

(52) U.S. Cl. ............... 374/33; 374/38; 374/43; 436/147

(58) Field of Classification Search ........... 374/34, 374/33, 31, 38, 36, 37; 422/51; 436/147; G01K 17/04
See application file for complete search history.

(56) References Cited

U.S. PATENT DOCUMENTS

| | | | | |
|---|---|---|---|---|
| 3,365,944 A | * | 1/1968 | Hoagland et al. | 374/34 |
| 3,593,577 A | * | 7/1971 | Monner | 374/34 |
| 4,130,016 A | * | 12/1978 | Walker | 374/34 |
| 4,439,048 A | * | 3/1984 | Townsend et al. | 374/34 |
| 4,670,404 A | * | 6/1987 | Swift et al. | 374/34 |
| 4,923,306 A | * | 5/1990 | Fauske | 374/34 |
| 5,547,282 A | * | 8/1996 | Pinhack et al. | 374/34 |
| 6,157,009 A | * | 12/2000 | Fauske et al. | 374/31 |
| 6,489,168 B1 | * | 12/2002 | Wang et al. | 436/147 |
| 2003/0058918 A1 | * | 3/2003 | Fischer et al. | 374/31 |

* cited by examiner

*Primary Examiner*—Diego Gutierrez
*Assistant Examiner*—Stanley J. Pruchnic, Jr.
(74) *Attorney, Agent, or Firm*—Francis H. Kirkpatrick; Kirk Patent Consulting

(57) ABSTRACT

A new adiabatic scanning calorimeter allows the thermal mass of a high-pressure reaction vessel to be dynamically compensated during a test. This allows the effective Φ factor for the experiment to be reduced to 1.0 without the use of complex pressure balancing equipment. Endothermic events can be quantified and sample specific heats can be measured. The time required for test completion is much shorter than for conventional adiabatic calorimeters, thus considerably improving apparatus productivity. The sensitivity to exotherm detection is at least as good as existing adiabatic calorimeters employing the Heat-Wait-Search strategy, but does depend on the temperature-scanning rate. In addition, the heat of reaction is obtained without reference to the heat capacity of the sample, pressure is measured continuously, reactants may be injected into the test vessel and the sample can be mixed during the test.

11 Claims, 9 Drawing Sheets

6 g 10% dtbp in 6 g Ti bomb with ramp heating and dynamic bomb compensation to Φ = 1.0

6 g 20% DTBP in Toluene in a 6 g Ti Bomb 6 g 20% DTBP in toluene in a 6 g titanium bomb 6 g 10% dtbp in 6 g Ti bomb with ramp heating and dynamic bomb compensation to Φ = 1.0

6 g DTBP (10% solution in toluene) in a 6 g titanium bomb, ramped at 0.5, 1.0, & 2.0 C/min and compensated to Φ = 1.0

3 Tests with 10% DTBP in a 6 g Ti bomb, a 10.5 g Ti bomb and a 18.4 g SS bomb, all compensated to Φ = 1.0

5.0 g 10% DTBP heated at 0.5 C/min in a 18 g 316 SS bomb
Bomb thermally compensated to $\Phi = 1.0$ 5 g 10.0% dtbp in a 18 g SS bomb ramped at 0.5 deg C/min and the bomb fully compensated for its mass($\Phi = 1.0$)

Heater energy as a function of sample temperature.
5g sample of 10% DTBP in a 18 g SS bomb.

4g NH4NO3 in a 10.6 g SS bomb heated at constant power (0.05 Watts)

4g NH4NO3 in a 10.6 g SS bomb heated at constant power (0.05 Watts)

3.0 g 10% $H_2O_2$ heated at 0.5 C/min in a 9.7 g 316 SS bomb and stirred at 200 rpm. Bomb thermally compensated to $\Phi = 1.0$ 4 g 16.7% dtbp in a 10.6 g SS bomb ramped at 2.0 deg C/min and the bomb compensated for 60% of its mass($\Phi = 1.25$)

3.0 g 16.7% DTBP in a 71g Hasteloy C bomb and stirred at 200 rpm.

3 g 16.7% solution DTBP in Toluene heated at 0.25, 0.5, 1.0 and 2.0 C/min in a 71 g Hasteloy C bomb and stirred at 200 rpm.

3.0 g 6.2% $H_2O_2$ heated at 0.5 C/min in a 71 g Hasteloy C bomb and stirred at 200 rpm.

3.0 g 6.2% $H_2O_2$ heated at 0.5 C/min in a 71 g Hasteloy C bomb and stirred at 200 rpm.

LOW THERMAL INERTIA SCANNING ADIABATIC CALORIMETER

This application claims the benefit of the priority of U.S. provisional application 60/485,949, filed Jul. 10, 2003, which is hereby incorporated by reference where permitted.

Thermal stability of materials, exothermic reactions, and thermal runaway are very often studied in the Accelerating Rate Calorimeter, more often referred to as the ARC®. Scientists at Dow Chemical first developed this device in the late 1970s and many papers describing the use of the ARC have since been written (1,2,3). Using this apparatus, a sample and a sample bomb are heated to a temperature where exothermic activity is detected in the sample by observation of the rate of temperature change of the sample. The sample and bomb are prevented from losing heat to the environment by careful control of guard heaters surrounding the sample bomb. A heating algorithm, commonly referred to as the Heat-Wait-Search™ (HWS) strategy, is used to control the initial heating of the sample and to bring the sample to a stable temperature during the exotherm search period.

FIG. 1 illustrates the HWS strategy and the use of the new, TIAX manufactured ARC to obtain heat of decomposition and reaction kinetics on a sample of di-tert-butyl-peroxide in a lightweight, spherical, titanium bomb. In this experiment 6 grams of a 20% solution of DTBP in toluene was heated in a 6 gram titanium bomb to an initial starting temperature of 95° C. An exotherm was detected at 110.5° C. after several heating steps and followed adiabatically to reaction completion. (Note the "steps" at the left and right sides of the scan.) The heat of decomposition was estimated at 49.35 Kcal/mol of DTBP using an average heat capacity of 0.51 cal/g ° C. for the sample solution and 0.135 cal/g ° C. for the titanium bomb. FIG. 2 shows the heating rate and pressure rate of the sample as a function of reciprocal temperature and also the $1^{st}$ order reaction rate for the decomposition reaction, as calculated from the exotherm portion of the heat rate plot (1). The activation energy and pre-exponential factor for the reaction agree well with published data (2).

While the ARC is a sensitive and stable adiabatic calorimeter, it suffers from a number of significant drawbacks.

- The thermal mass of the sample bomb is often large in comparison to the sample such that a large fraction of the heat released by the sample is absorbed by the bomb, resulting in lowered peak reaction temperatures and pressures. In other words, most tests are run with a relatively large Φ factor.
- The heaters on the older style ARCs are confined to a temperature rate below about 15 ° C./min, although the newer TIAX ARC is capable of tracking heat rates to 250 C./min. This greater tracking rate is, of course, only of utility if the sample and bomb are in thermal equilibrium throughout the exotherm.
- The time required to complete a test using the HWS strategy often exceeds twenty-four hours so that productivity per machine is very low.
- The apparatus is not capable of quantifying endothermic behavior.
- Stirring, on the older style ARCs, although possible, is very expensive and therefore not often used.

In the early 1980s, the DIERS Bench Scale Apparatus was developed and commercialized by Fauske and Associates (4,5) as the VSP™. The apparatus was designed to characterize chemical systems subject to thermal runaway and to calculate a vent size for a particular reactor from measurements of the temperature and pressure rates made in the apparatus. This device overcame the main disadvantage of the ARC, the high Φ factor, but at a cost of loss of sensitivity. In addition, a relatively large sample size was required and the device required complex, high-pressure plumbing and a 'containment vessel' for the pressure balancing system. Competitive machines such as the APTAC™ (6,9) and the Phi-Tec™ (7) also suffered from similar disadvantages, although the APTAC does retain the sensitivity of the ARC.

The differential scanning calorimeter (DSC) is also extensively used for obtaining information on thermal events in materials. However, pressure measurements are not usually made due to the small sample size employed (~1–20 mg). Also, reactant addition during the test and sample stirring are problematic with the DSC and because it is a scanning method at a constant heat rate, the data cannot be easily scaled to full size equipment which may be handling or storing the material being tested.

SUMMARY OF THE INVENTION

An improved calorimeter using a new adiabatic technique has been developed. The technique may be embodied in new calorimeters. In some cases, existing equipment can be modified to allow use of the new techniques, although the advantages of using the method on older machines may be limited by the small maximum heating rate the machines can accurately track.

In one aspect, the improved calorimeter comprises a sample bomb and a bomb thermocouple, one or more guard heaters and thermocouples for the guard heaters and optionally a thermocouple for the sample. The sample bomb is equipped with a sample heater positioned inside the bomb, or in or on the wall of the bomb itself or in or on the wall of an associated heat sink. The sample heater, regulated by a controller via feedback from one or more thermocouples, emits heat into the sample at a rate that is programmed to increase the temperature of the sample and of the bomb at a constant preselected rate.

In another aspect of the invention, the heat output of the sample heater is decreased during sample exotherms, and increased during sample endotherms, to maintain the selected rate.

In another aspect, the improved calorimeter has provisions to input heat into the sample at a rate proportional to the heating rate of the sample in order to compensate for the heat loss from the sample to the sample bomb during an exothermic reaction.

In another aspect, the sample heater may be placed outside the sample in a heat sink which is in good thermal contact with the bomb. Using this configuration, the sample heating rate is controlled at a constant rate throughout the exotherm.

In another aspect, the calorimeter may contain more than one bomb, each bomb having an associated sample heater and bomb thermocouple such that several samples may be simultaneously scanned at the same temperature rate in the same adiabatic environment.

In another aspect, the apparatus further comprises one or more of a pressure sensor, a stirring motor or other stirring device, and a cooling capacity allowing measurements to begin at sub-ambient temperatures.

In another aspect, the calorimeter may have only one thermocouple, other than guard heater thermocouples, to estimate the sample and bomb temperature.

Further aspects of the invention will be evident from the description.

DETAILED DESCRIPTION OF THE INVENTION

The invention comprises both an improved calorimeter, and improved measurements and measurement techniques that are made possible by the improved calorimeter.

1. The Calorimeter

Figure 1:
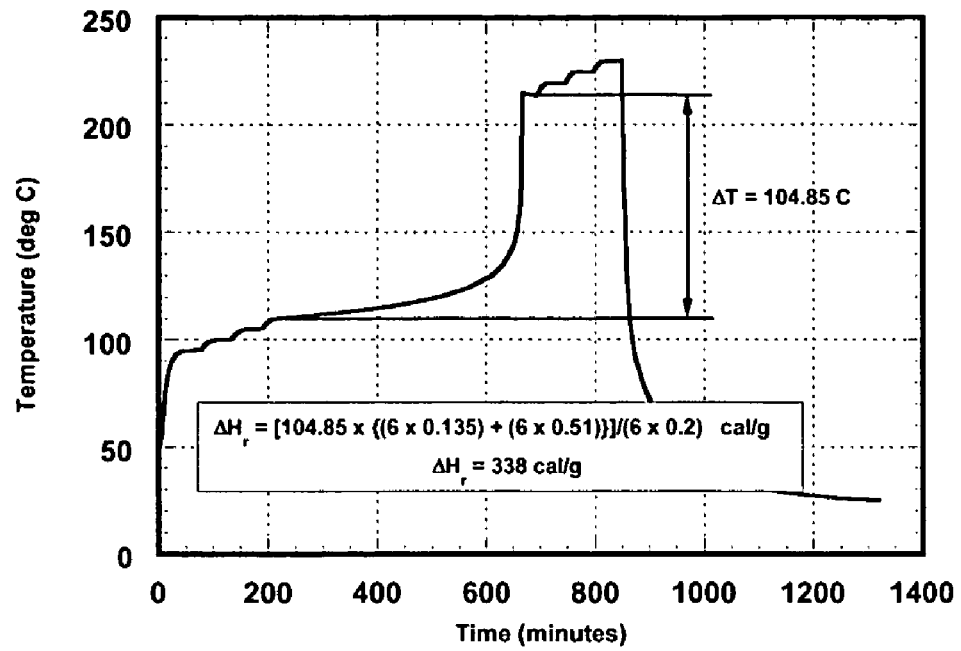
FIGS. 1 and 2 show tests with a model substance (DTBP; di-tert-butyl peroxide) in a prior art ARC machine.
Figure 2:
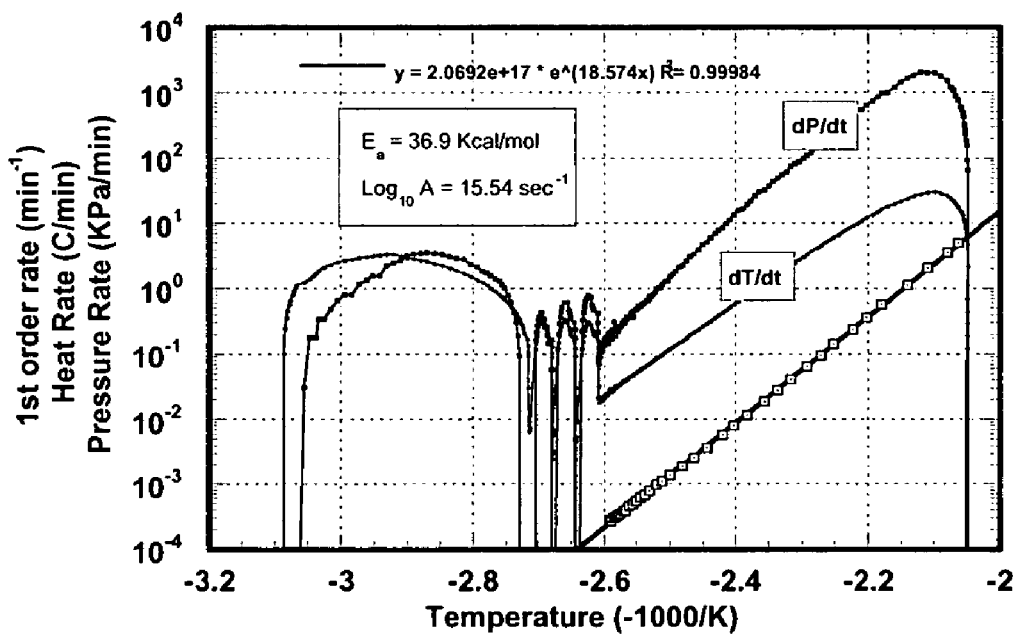
Figure 3:
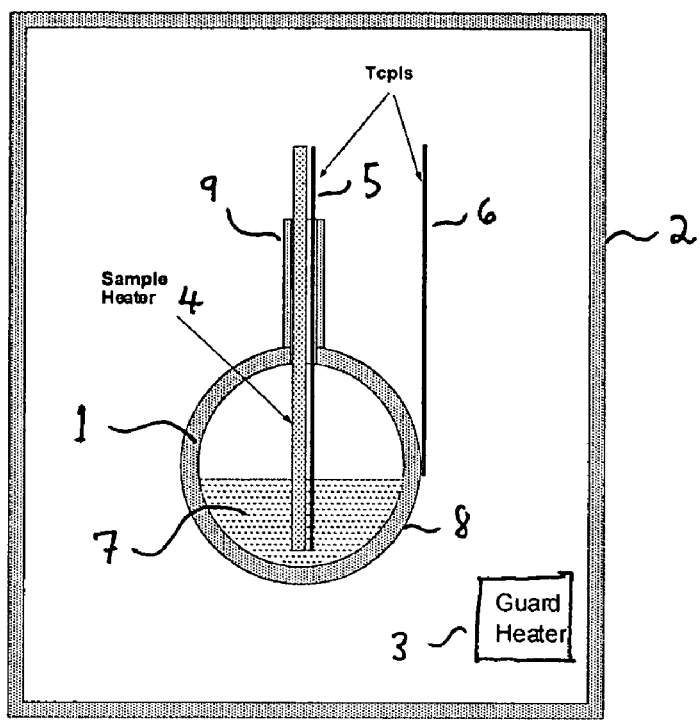
FIG. 3 is a schematic drawing of the improved calorimeter of the invention.

The calorimeter is shown schematically in FIG. 3. The calorimeter comprises a sample reaction vessel or bomb 1, an enclosure 2, guard heaters 3 connected to enclosure 2, sample heater 4, first (outer bomb) thermocouple 6, optional second (sample) thermocouple 5, sample 7, and outer surface 8 of the bomb 1. Each of the guard heaters 3, of which there are typically one to four, has an associated thermocouple (not shown). Each of the several thermocouples provides data to a controller (not illustrated). The controller regulates the amount of heat provided by the sample heater 4 and each guard heater 3. The controller also records the data from the thermocouples and performs calculations to select the amount of power to be provided to the sample heater 4 and the guard heaters 3.

The guard heaters 3 are typically wound as coils around an enclosure 2 which fits closely around the bomb 1. They may also be formed as a coil on a lid of the apparatus or the enclosure 2 (not illustrated). In some embodiments, a guard heater coil is wound around the upper end of the "stem" 9 of the bomb to prevent heat leakage by conduction. In operation, a particular rate of temperature increase that is to be applied to the sample is selected. The sample heating rate is detected by the sample thermocouple 5 and the first, outer bomb wall thermocouple 6. The power supplied to the sample heater 4 is regulated to obtain the desired rate of heating.

Meanwhile, the first, outer thermocouple 6 senses the outside temperature of the bomb 1. The guard heater 3 temperature is controlled at the same temperature as the temperature of the outside surface 8 of the bomb wall in order to maintain adiabatic conditions around the sample bomb 1.

In an alternative mode, the sample 7 temperature may be estimated from the measured temperature and rate of temperature rise of the outer bomb wall 8, thus eliminating the need for the sample thermocouple. In addition, in this alternative mode the bomb wall thickness and thermal conductivity are preferably known, relative to a standard bomb which has been calibrated in a prior experiment.

At some temperature (or more than one), the sample 4 will undergo a change. This may be an endothermic change, such as a melting or a phase transition; or it may be an exothermic change, which can be a phase transition or can be a decomposition or other chemical change.

When the change is an endotherm, the sample heater power output is increased to keep the rate of temperature rise constant. Alternatively, and preferably, the applied sample heater power may be controlled at a constant rate during an endotherm. Under these conditions, the rate of temperature rise of the sample will fall toward zero and the guard heaters surrounding the sample bomb will maintain adiabatic conditions.

When the change is an exotherm, the power supplied to the sample heater is decreased to keep the sample temperature rate constant. The rate of heat loss from the sample to the sample bomb is continuously calculated. When the sample heater power output has decreased to equal the heat loss rate to the sample bomb, the sample power output is adjusted to be equal to the heat loss rate to the sample bomb for the remaining duration of the exotherm, thus eliminating the effect of the mass of the bomb on the course of the exothermic reaction. Under these circumstances, the sample heating rate will accelerate above the initially controlled, steady state heating rate. The guard heater temperature rate is also increased to maintain adiabatic conditions around the sample bomb. In an alternative mode, several sample bombs 1, optionally surrounded by heat sinks 11 may be heated at the same rate of temperature rise within the adiabatically controlled heated space surrounding the sample bombs. In this configuration, each sample and heat sink has a separately controlled sample heater so that multiple samples may be simultaneously tested in the apparatus.

2. Temperature Scanning Tests with Dynamic Compensation for Bomb Wall Heat Losses The many potential sources of heat loss from a sample in an adiabatic environment include:
  Conduction up the stem 9 of the reaction vessel (bomb) 1 and along the thermocouple sheath (not illustrated).
  Convection losses from the surface 8 of the bomb 1
  Radiation exchange with the surrounding heaters 3
  Refluxing by vapor condensation on an optional fitting which seals the reactor and connects it to the pressure transducer (not illustrated.)

A well-designed adiabatic calorimeter will minimize the source of these losses (or gains) and the TIAX ARC achieves excellent adiabaticity by good design, good control algorithms and automated thermocouple calibration checks. However, a further source of loss is heat loss to the bomb wall from the reacting sample.

Traditionally, the relative loss to the bomb wall is described by the $\Phi$ factor, defined as $$\Phi = 1.0 + M_b C_b / M_s C_s \qquad [1]$$

where M is mass, C is heat capacity and the subscripts b and s refer to the sample bomb and the sample respectively. Generally, $\Phi$ factors for experimental adiabatic calorimeters tend to be about 1.5–3.0 because the reaction vessel needs to be strong enough to contain the reaction products at high temperature and pressure. A large fraction of the reaction energy is therefore absorbed by the reaction vessel, which significantly changes the temperature and pressure-time histories. A Φ factor of 2.0, for instance, means that one half the reaction heat will be absorbed by the bomb. The ARC manages a heavy walled bomb by keeping the 'system' adiabatic where the system is the sample and the bomb. In this case, the sample and the bomb must be at the same temperature throughout the exotherm. In the event that the sample temperature rises significantly above the bomb wall temperature the data will be subject to serious errors.

Bomb wall losses are minimized in the APTAC, VSP and Phi-Tec by using thin walled bombs that have a very small thermal mass relative to the sample, so that the Φ factor is approximately 1.1 or less. However, a number of disadvantages arise from using a thin-walled reaction vessel, including:

A pressure containment vessel and associated pressure balancing system is typically required to prevent bomb rupture.

It is difficult to control heat losses from the sample as the pressure changes, sometimes very rapidly, within the containment vessel.

There are practical limitations to the rate of pressure rise that can be 'balanced', arising from the control of the rate of flow of inert gas to the containment vessel.

Bomb rupture is not infrequent, leading to messy clean-ups and downtime while the machine is cleaned and re-calibrated.

An alternative method to account for the mass of the reaction vessel during an adiabatic experiment has been developed. The method involves the use of a small, computer controlled, heater immersed in the sample. Software continuously calculates the heat lost to the bomb from the sample during an exothermic event. The power from the heater is controlled to equal the rate of heat loss from the sample to the bomb. Thus, the net heat loss is zero. Using the same heater it is also possible to measure energy absorbed by the sample during the heat up phase of the experiment and therefore to calculate a heat capacity for the sample or to quantify any endothermic activity which takes place in the sample.

FIG. 3 represents a heavy walled sample reaction vessel 1 in an adiabatic environment inside an enclosuere 2. The temperature of the sample 7, $T_s$, is measured using an optional but preferred thermocouple 5 (called the "second" thermocouple), and the temperature of the exterior wall of the sample vessel, $T_w$, is measured using a first thermocouple 6. The sample 7 and the reaction vessel 1 are heated at a constant rate by a small heater 4 in contact with the sample 7. The heating rate is chosen such that the sample temperature, $T_s$, is essentially at the same temperature, $T_w$, as the outside wall 8 of the bomb 1. Guard heaters 3 surrounding the reaction vessel prevent any heat losses from the system by conduction, radiation or convection. If the sample 7 begins to evolve heat, the sample heater 4 is controlled such that the overall rate of temperature rise remains constant. If the sample exhibits endothermic behavior, the sample heater 4 output is increased to keep the temperature rate constant.

To analyse the experimental data, the following assumptions are made in the equations and procedures below, unless otherwise stated:

The sample is at a uniform temperature.

The inside bomb wall temperature is uniform over the entire inner surface area and the outside bomb wall temperature is also uniform although not necessarily equal to the inner surface temperature.

The inside wall temperature of the reaction vessel is the same as the bulk liquid temperature at all times.

Heat losses at the outside wall of the sample bomb are zero.

The wall thickness of the sample bomb is constant throughout the vessel.

Initially the sample heater 4 heats the sample 7. Some of the heat is transferred to the bomb 1 walls so that the heater effectively heats both the sample and bomb. Since the bomb is heated entirely by the sample, the rate of heat loss from the sample to the bomb is given by $$dQ_L/dt = 0.57302 M_b C_b (dT_w/dt + dT_s/dt) \quad [2]$$

where $0.5(T_w+T_s)$ is the average bomb temperature. It follows, therefore, that adding heat to the sample at the rate given by equation [2] will compensate for wall heat losses during the exothermic portion of the experiment.

In order to achieve the goal of eliminating wall heat losses, the following experimental requirements are necessary:

The assumptions listed above are valid.

Accurate measurement of the inside and outside bomb wall temperatures are obtained.

Heat losses from the system (consisting of the sample and the reaction vessel) by convection, radiation, conduction and refluxing are eliminated.

Guard heaters surrounding the sample bomb are capable of tracking the increased sample heating rate which is observed when bomb heat losses are eliminated or reduced.

A computer controlled heater is in good thermal contact with the sample, and is capable of delivering power at the rate given by the above expression.

Good heat transfer is present between the sample and the bomb. For liquid samples that evolve heat at a rapid rate this can mean that stirring of the sample is necessary.

Good heat transfer is present between the heater and the sample, which may require sample stirring for liquid samples evolving heat rapidly.

High viscosity liquids and solids can also be measured if heating rates are kept low. Solid, particulate materials and high viscosity liquids would tend to decrease the heat transfer rate from the heater to the material and also from the material to the interior wall of the sample bomb. Heating rates must necessarily then be kept lower in order to ensure adequate thermal equilibrium throughout the system.

2.1 Controlling the Φ Factor

Equation 2 above may be modified by the factor λ, representing the fraction of the mass of the bomb that is to be compensated by addition of heat from the sample heater. The factor λ varies from zero where no compensation occurs to unity where the mass of the bomb is fully compensated.

$$dQ/dt = 0.5 \lambda M_b C_b (dT_w/dt + dT_s/dt) \quad [3]$$

It is therefore possible to control the rate of heat added to the system for any desired Φ factor from 1.0 to an upper limit set by the total mass of the bomb and the mass of the sample, as given by equation [1] above.

Since the sample temperature and the outside bomb wall temperature will tend to diverge during an exotherm, it is important to choose the correct temperature to represent the sample temperature. If the heat loss compensation is zero then the relevant temperature to use for the 'sample' will be the outside wall temperature, as in a prior art ARC experiment. This temperature should be essentially the same as the inside wall temperature. If the heat loss compensation is such that the effective Φ for the experiment is greater than 1.0, then the temperature to use will be the temperature of the sample liquid, or of the inside bomb wall.

In practice, the sample and the bomb are initially heated at a constant heating rate using the sample heater. Heat losses are prevented by careful control of the environmental temperature. At some point during the temperature scan the sample will typically begin to evolve heat. The heater output is then adjusted (reduced) sufficiently to control the heating rate at the initial set rate. During this time period the sensible heat stored in the sample and the sample bomb has therefore partly come from the sample and partly from the heater. When the heater output reaches the level required to fully compensate for the thermal inertia of the bomb, as given by equation [3], the system temperature rate is allowed to accelerate and the heater output is controlled according to equation [3].

Exotherm onset can be detected at lower temperatures, depending on the initial temperature scan rate.

2.2 Experimental

A number of experiments using DTBP solutions were run to demonstrate the utility of the method. Table 1 lists the tests and summarizes the results. During the portion of the test where the sample heater was used to compensate for the thermal mass of the bomb, the heat capacities of the bombs were assumed to be a function of the temperature and were calculated as follows (Ref. 12):

Titanium: $C_p=0.10105+0.00006788.T$

Stainless Steel: $C_p=0.07390+0.00011420.T$

Hasteloy C: $C_p=0.08681+0.00003000.T$ where the temperature T is the average bomb wall temperature, in degree Kelvin, obtained from measurements of the inside wall temperature (which is the same as the sample temperature) and the outside wall temperature.

TABLE 1

Summary of tests with DTBP solution and thermal compensation of sample bomb

| Conc. (%) | Sample Mass (g) | Bomb Type | Bomb Mass (g) | Scan Rate (C/min) | λ | ΔH$_r$ (Cal/g) | E$_a$ (Kcal/mol) | Log$_{10}$[A] (sec$^{-1}$) |
|---|---|---|---|---|---|---|---|---|
| 20.0 | 6.0 | Ti | 6.0 | HWS | 1.26* | 338 | 36.9 | 15.54 |
| 16.7 | 3.0 | SS | 9.8 | 1.0 | 1.0 | 342 | 36.52 | 15.28 |
| 16.7 | 4.0 | SS | 10.6 | 0.25 | 1.0 | 342 | 36.44 | 15.33 |
| 16.7 | 4.0 | SS | 10.6 | 0.5 | 0.0 | 354 | 37.48 | 15.8 |
| 16.7 | 4.0 | SS | 10.6 | 1.0 | 0.6 | 347 | 36.36 | 15.27 |
| 16.7 | 4.0 | SS | 10.6 | 1.0 | 0.75 | 367 | 37.2 | 15.69 |
| 16.7 | 4.0 | SS | 10.6 | 2.0 | 0.6 | 369 | 36.62 | 15.4 |
| 16.7 | 4.0 | SS | 6.35 | 1.0 | 0.6 | 357 | 37.4 | 15.75 |
| 16.7 | 4.0 | Ti | 6.0 | 0.5 | 1.0 | — | 36.55 | 15.3 |
| 10.0 | 5.0 | Ti | 10.5 | 0.5 | 1.0 | 339 | 37.27 | 15.67 |
| 10.0 | 5.0 | Ti | 18.4 | 0.5 | 1.0 | 349 | 36.56 | 15.3 |
| 10.0 | 5.0 | SS | 18.5 | 0.25 | 1.0 | 354 | 36.6 | 15.28 |
| 10.0 | 5.0 | SS | 18.5 | 0.5 | 1.0 | 353 | 36.71 | 15.6 |
| 10.0 | 5.0 | SS | 18.5 | 1.0 | 1.0 | 352 | 37.13 | 15.43 |
| 10.0 | 5.0 | SS | 18.5 | 2.0 | 1.0 | 379 | 36.48 | 15.27 |
| 10.0 | 5.0 | SS | 18.5 | 0.25 | 0.0 | 376 | 36.48 | 15.28 |
| 10.0 | 6.0 | Ti | 6.0 | 0.5 | 1.0 | — | 36.67 | 15.36 |
| 10.0 | 6.0 | Ti | 6.0 | 1.0 | 1.0 | — | 36.06 | 15.07 |
| 10.0 | 6.0 | Ti | 6.0 | 2.0 | 1.0 | — | 36.05 | 15.05 |
|  |  |  |  | AVERAGE |  | 355.7 | 36.76 | 15.44 |

*This number is the Φ factor and does not refer to the value λ for this particular test. Also the data were not included in calculating the average values for E, A and ΔH.

The advantages of using this type of test over the more traditional ARC method include:

- The test time is considerably shortened since the slow HWS portion of the test is eliminated. (It is not necessary to step and wait for equilibrium.)
- Data can be obtained at Φ factors ranging from 1.0 to the maximum value possible for a bomb of any given mass.
- The heat of reaction can be obtained without reference to the heat capacity of the sample, as explained in section 2.3 below
- It is possible to add excess heat to the bomb in a controlled fashion and thus simulate fire exposure to a vessel containing thermally unstable material.
- Heat capacities of the reactants and products of the reaction can be measured from the known heat input before and after the reaction the relatively small thermal conductivity of the steel. Because this method uses a controlled sample heater, it is possible to quantify the rate of heat loss to the fitting under different conditions.

In order to minimize conduction heat losses during a transient temperature change, the heater to which the fitting is attached is run at a slightly higher temperature than the temperature of the sample bomb. The temperature elevation is dependent on the rate of temperature scan at which the test is run. The magnitude of the temperature elevation is obtained in a prior calibration test using water in a sample bomb and heating the system at a number of temperature rates. The heater temperature elevation is adjusted until the correct value of the heat capacity of the known mass of water is obtained. It was found that the required temperature elevation could be expressed by an equation of the type:

$$\Delta T = a \, [dT_w/dt]^b$$

with the stipulation that the maximum elevation is 10° C. It was also found that the values of the constant, a, and the exponent, b, were somewhat dependent on the size of the stainless steel fitting. Although no other fittings than 316 stainless steel were used, the values would also be expected to depend on the material of construction of the fitting, which affect the heat capacity and the thermal conductivity and therefore the rate of heat loss to the fitting at any given heat rate.

2.2.2 Tests at Different Temperature Scanning Rates but in the Same Mass Bomb.

Figure 4:
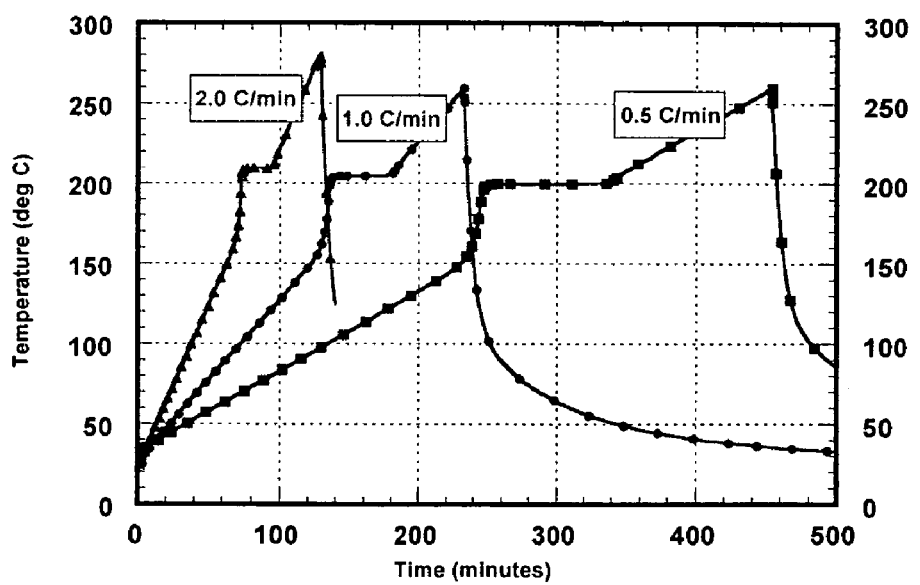
FIGS. 4, 5 and 6 show plots with DTBP on the new apparatus.
Figure 5:
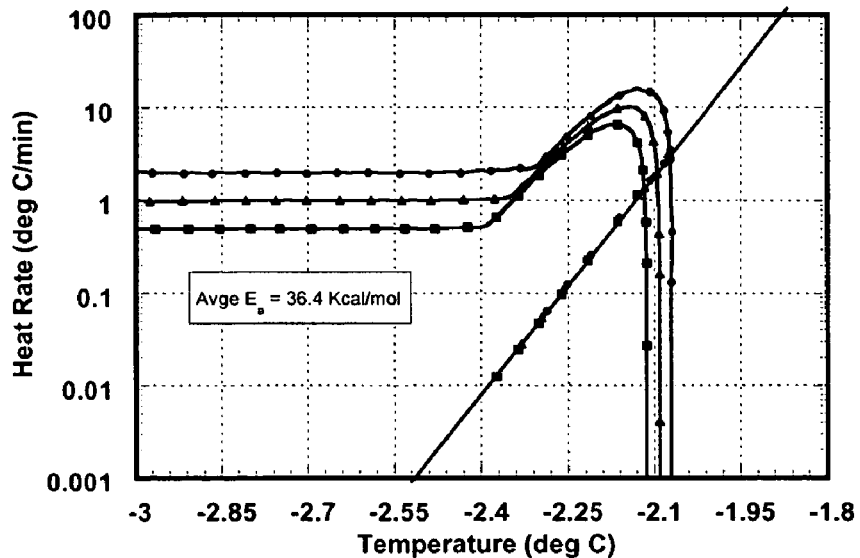

FIG. 4 shows the temperature-time profiles for three tests using a 10% solution in a 6 gram titanium bomb and heated at 0.5, 1.0 and 2.0° C./min. The first and later portions of each temperature-time plot represent forced heating of the sample and bomb at a constant rate. It is possible to extract heat capacity estimates from this data since the heater energy required to heat the system is known. The central portion of each plot is the temperature rise associated with the exothermic decomposition of the DTBP. During this part of the test the thermal mass of the bomb is totally compensated by addition of heat to the sample at a rate given by equation [3]. This is more clearly shown in FIG. 5 where the logarithm of the heating rate is plotted as a function of reciprocal temperature. As expected, the maximum rate of self-heating and the peak temperature of the exotherm are increased as the forced heating rate during the initial heating stage is increased. The average value for activation energy for this series of tests was 36.4 Kcal/mol. This compared favorably with the value in Ref (7) where the average of sixteen runs from a Round Robin in the VSP apparatus was reported as 36.1±1.0 Kcal/mol. However, this value is a little lower than that reported in Ref (2) where a value of 37.8±1.1 Kcal/mol was found from tests conducted in an ARC.

2.2.3 Tests at Same Temperature Scanning Rates but in Different Bombs.

Figure 6:
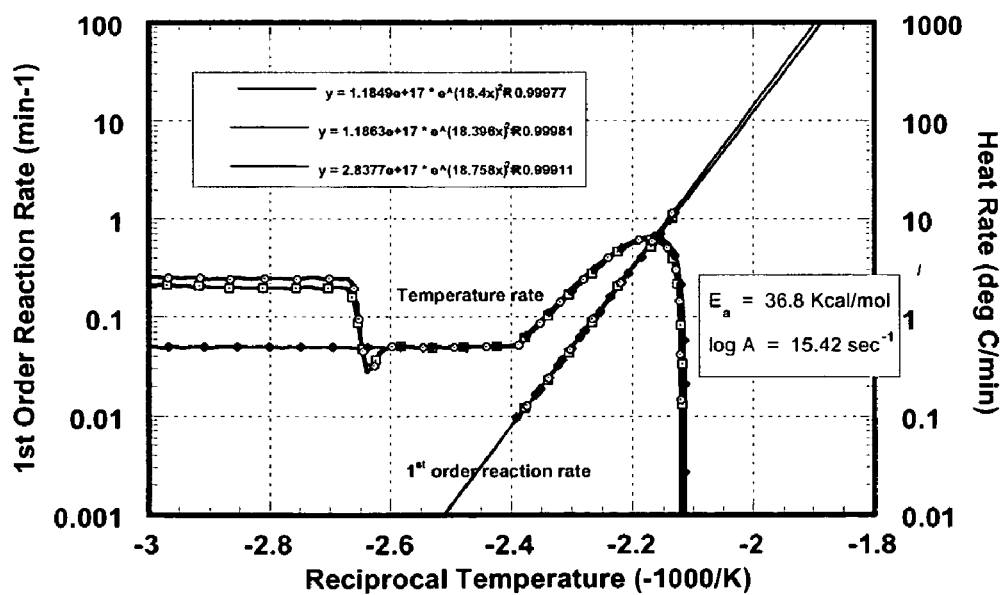

A second series of tests was run using the same solution but in bombs of differing mass. For the three bombs used in the experiments, the uncompensated Φ factors were 1.26, 1.54 and 1.88. FIG. 6 is a plot of the self-heating rate and the first order rate, k, for the decomposition where the rate is calculated from the self-heat rate and the temperature rise for the sample (see ref (1) and discussion under 'Activation Energy' below). The first order rate and subsequently the activation energy and pre-exponential factors for all tests listed in Table 1 were calculated from equation [4] using the data measured during the bomb compensation phase of the experiment.

$$k = (dT/dt)/(T_f - T) \qquad [4]$$

The calculated kinetic parameters for the three tests are in excellent agreement and similar to the values published in the literature. Clearly, the sample heater has adequately compensated for the masses of the three different bombs, as evidenced by the virtually identical self-heat rate plots for the three tests. Note that in two of the tests, the initial heating rate of the sample was increased in order to decrease the overall test time. Prior to the detected onset of the exotherm, the heating rate was lowered to the desired temperature scan rate of 0.5° C./min.

2.3 Reaction Energy and Power

Referring again to FIG. [3], a simple heat balance on the system gives the following expression $$W + H = S + B \qquad [5]$$

where W is the energy released or absorbed by the sample, H is the energy output by the heater, S is the sensible energy in the sample and B is the sensible energy in the bomb. The expression assumes that there are zero energy losses from the bomb and sample.

Therefore, the energy released from the sample is given by $$W = S + B - H \qquad [6]$$

and the sample power output is given by $$dW/dt = dS/dt + dB/dt - dH/dt \qquad [7]$$

or $$dW/dt = M_s C_s (dT_s/dt) + 0.5 M_b C_b \{(dT_w/dt) + (dT_s/dt)\} - P \qquad [8]$$

where P is the power output of the heater. If the test is run at a small and constant heating rate, it may be assumed that $(dT_s/dt) = (dT_w/dt)$ and therefore $$dW/dt = (M_s C_s + M_b C_b) \cdot (dT_w/dt) - P \qquad [9]$$

The expression enables the calculation of the energy and power output from the sample as a function of temperature provided that the heat capacities of the sample and the bomb are known. Alternatively, if there is no exothermic heating, then the heat capacity of the sample may be determined, as a function of temperature, if the heat capacity of the sample bomb is known or has been measured in a prior experiment. If the heat capacities of the sample and the bomb are both unknowns the combined heat capacities are directly measured prior to and after any exothermic or endothermic behavior. The quantity $[(M_s C_s + M_b C_b) \cdot (dT_w/dt)]$ is measured as baseline power output, $P_0$, from the sample heater and is the power required to heat the sample and the sample container at the given temperature scanning rate. Equation [9] may therefore be rewritten as:

$$dW/dt = P_0 - P \qquad [10]$$

If the sample heat rate exceeds the base line rate and (dT.sub.s/dt)(dT.sub.w/dt), then the equation must be modified to:

$$dW/dt = \{P_0(dT.sub.s/dt)/(dT.sub.0/dt)\} - 0.5 M.sub.b C.sub.b\{(dT.sub.s/dt) - (dT.sub.w/dt)\} - P \qquad [10a]$$

where $(dT_s/dt)$ is the measured sample heat rate and $(dT_0/dt)$ is the base line heating rate. Equation [10a] reduces to equation [10] when $(dT_s/dt) = (dT_w/dt) = (dT_0/dt)$. In other words, when the temperature rate is kept constant throughout the test. The heat of reaction, $\Delta H_R$, is given by the integral of dW/dt.

$$\Delta W = \int (P_0 - P) \cdot dt = \Delta H_R \qquad [11]$$

Note that this expression does not require a knowledge of the heat capacity of the sample in order to obtain a measurement of the heat of reaction, unlike a traditional ARC experiment where an adiabatic temperature rise is measured and heat of reaction can only be obtained if the average heat capacity of the sample over the temperature range of the experiment is known. However, if the bomb is thermally compensated during the exotherm portion of the test using equation [3], then a prior knowledge of the heat capacity of the sample bomb is required in order to correctly control the heater output. In addition, if the sample heat rate becomes large due to the thermal compensation, then the condition that $(dT_s/dt) = (dT_w/dt)$ will no longer be true, especially if the bomb wall thickness is large. The sample power output should then be calculated using equation [8]. For these cases the heat capacities of the sample and the bomb need to be known or obtained from the non-exothermic heating portion of the experiment.

2.4 Activation Energy

The kinetics for simple reactions may be obtained in a manner analogous to the method used in traditional ARC experiments and described in Ref(1). For an $n^{th}$ order reaction with a single reactant the rate of reaction is $$dC/dt = -kC^n \quad [12]$$

By assuming that the concentration of the reactants at any temperature can be related to the energy change, $$C/C_0 = (W_f - W)/\Delta W \quad [13]$$

an expression can be derived which relates the measured energy output to the kinetics. In the expression above, C is the concentration of a single reactant at any temperature, $C_0$ is the initial concentration, $W_f$ is the final energy output level due to the reaction, W is the energy output at any temperature and $\Delta W$ is the total energy output due to reaction. If this expression is differentiated with respect to time, t, and substituted into equation [12] then $$dW/dt = k \cdot C_0^{n-1} \cdot [\{(W_f - W)/\Delta W\}^n \Delta W] \quad [14]$$

and using the Arrhenius equation:

$$k = Ae^{-(E/RT)} \quad [15]$$

where A is the pre-exponential factor and E the activation energy and R is the gas constant, the expression $$ln\{(dW/dt)/[\{(W_f - W)/\Delta W\}^n \Delta W]\} = ln\ C_0^{n-1} A - E/RT \quad [16]$$

is derived. Therefore, plotting the logarithm of the measurable quantities on the left-hand side of the equation versus reciprocal temperature yields a straight line if the correct order, n, is chosen for the reaction. The activation energy and pre-exponential factors may be calculated from the slope and intercept respectively.

The use of equations [9], [10], [11] and [16] allow the early detection of an exothermic event during the time period when the heating rate is constant. Moreover, the heat output from the reaction is continuously summed during the scanning period.

The use of these equations is demonstrated in the following experiment. Five grams of a 10% solution of DTBP in toluene was heated at 0.5° C./min in a 18 gram stainless steel reaction vessel. At about 145° C., the power output from the heater was the same as that required to fully compensate for the thermal mass of the bomb at that heating rate. From this temperature until the completion of the exotherm at about 203° C., the power output of the heater was controlled by equation [3] with the value of λ set to 1.0. At 203° C. the heater power was adjusted to the power required to heat the system at the ramp rate using a PID control algorithm.

Figure 7:
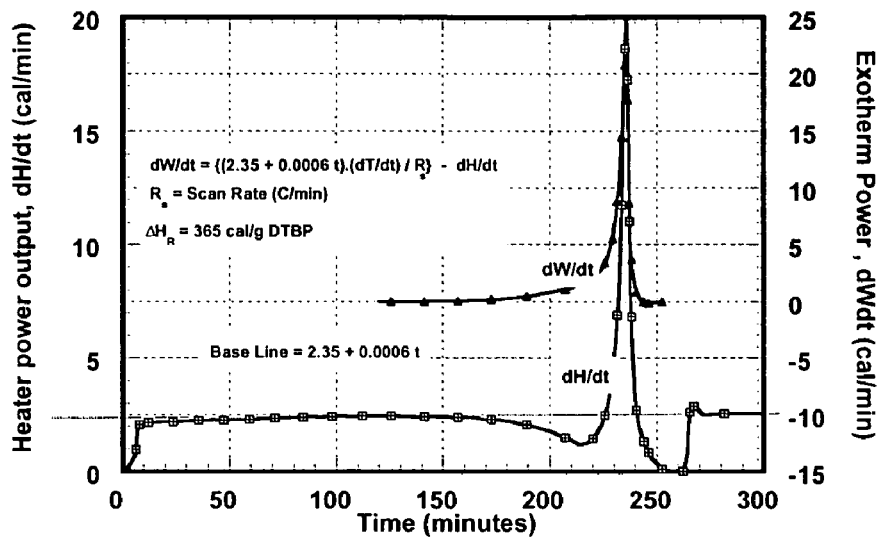
FIGS. 7 and 8 show different types of plots with the inventive apparatus for the model material.
Figure 8:
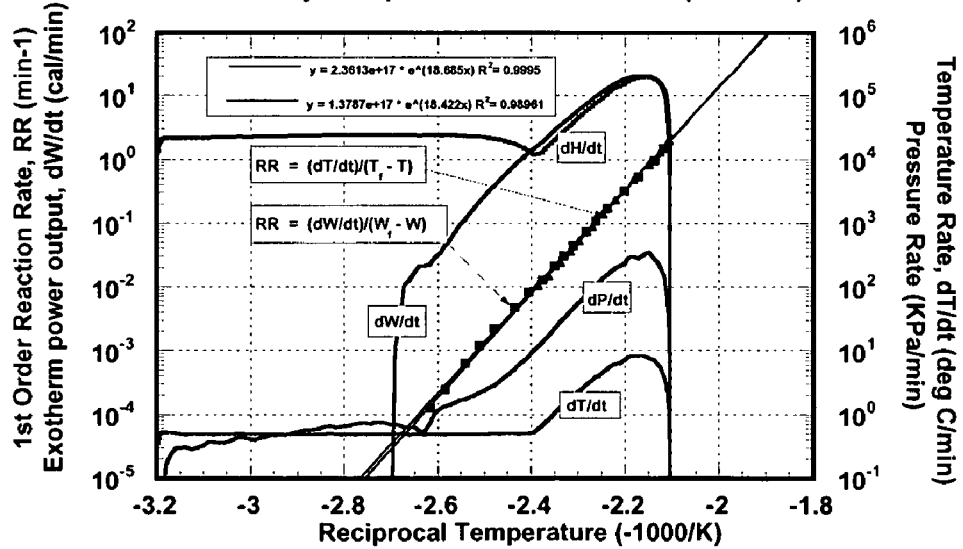

FIG. 7 shows the heater power output, dH/dt, and the sample power output, dW/dt, as a function of time. The sample power output was derived from the heater output curve in the following manner:

A straight base line was drawn on the heater power output curve from the start of the downward deviation on the power output to the point where the power from the heater is increased to a constant level after the exotherm, as shown in FIG. 7. This line represents the base line power output from the heater necessary to heat the reactants and the sample bomb at the experimental scan rate. The equation of the base line was found and substituted into equation [10a] for $P_0$ $$dW/dt = \{(2.35 + 0.0006 \cdot t) \cdot (dT_s/dt)/R_s\} - dH/dt - 0.5 M_b C_b \{dT_s/dt - dT_w/dt\} \quad [17]$$

where $R_s$ is the initial temperature scanning rate. Since the rates of temperature rise, $dT_s/dt$, $dT_w/dt$, and the heater power output, dH/dt were known throughout the experiment, the sample power output, dW/dt was calculated as a function of time (or temperature). Integration of this curve with respect to time yields the heat of decomposition of the DTBP. Substitution of equation [17] into equation [16] allows for the calculation of the kinetic parameters for the decomposition reaction. FIG. 8 is a logarithmic plot of the heater power output, the sample power output, the sample temperature rate and the rate of pressure rise as a function of reciprocal temperature. In addition two plots are shown on the graph which represent the $1^{st}$ order reaction rate constant calculated using equation [16] and also the same rate constant calculated using the temperature rate data after 145° C. and equation [4]. It is not possible to use the temperature rate data prior to 145° C. because the rate is constant and therefore no information can be extracted. The two lines give essentially the same activation energies and pre-exponential factors, as may be seen in the plot. The average value of the activation energy was found to be 36.88 Kcal/mol and the heat of reaction was 367 cal/g DTBP.

Note that the start of the exotherm can easily be detected at about 108° C. (−2.625 on the axis scale used in FIG. 8) using the sample power output plot. This temperature is about 7 degrees centigrade lower than the standard ARC detection limit for this reaction, despite the fact that this was a scanning test and did not make use of the HWS strategy which was thought to be the most sensitive way to run an adiabatic calorimeter. The method therefore, is not only considerably faster then the standard ARC method, but also is more sensitive, gives a heat of reaction without a knowledge of the heat capacity of the system and enables the test to be run at a Φ factor of 1.0

2.5 Calculation of the Apparent Specific Heat of the Sample.

Using the heater power output prior to any self-heating in the sample and also after exothermic activity has ceased, it is possible to estimate the heat capacity of the sample and the products of the reaction. Initially, the heater power is used to heat both the sample and bomb at the given temperature scan rate. If the system has been well calibrated and heat losses are zero, then the specific heat of the sample may be obtained as a function of temperature, provided that the specific heat and mass of the sample bomb are known.

Thus, from equation [9] and assuming that the sample power output, dW/dt, is zero $$P = (M_s C_s + M_b C_b) \cdot (dT_w/dt) \quad [18]$$

$$C_s = \{P/(dT_w/dt)\} - \{M_b C_b\}/M_s \quad [19]$$

Figure 9:
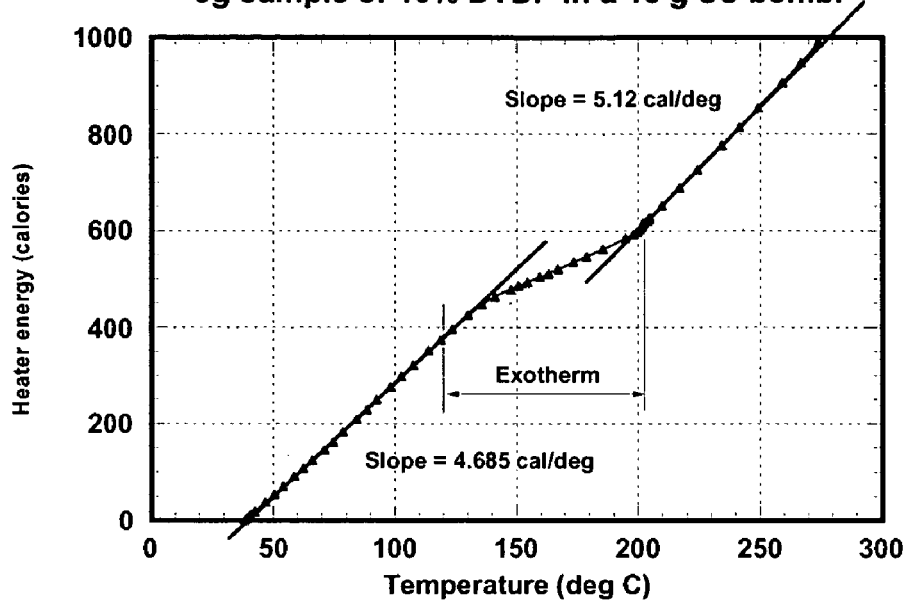
FIG. 9 shows the sample heater output during an exotherm.

This function is calculated by the control software and can be displayed graphically during the test. FIG. 9 shows a typical test result obtained on a sample of DTBP heated at 0.5° C./min in a 18 gram stainless steel bomb. The plot also shows that as the sample begins to evolve heat, the energy output from the heater decreases. The heat capacity of the system cannot be determined when the sample is thermally active. It has also been found that the function is very sensitive to the temperature of the top heater. The top heater is used to heat the high-pressure fitting to which the sample bomb is attached. Therefore, very small heat losses to the fitting can affect the estimated value of the specific heat, especially if the sample mass is small and the sample bomb mass is relatively large. From the slopes of the lines before the exotherm in FIG. 9 above, the average specific heat of the sample was determined to be 0.505 cal/g° C. The apparent value of the specific heat after completion of the decomposition was similarly determined to be 0.592 cal/g° C.

2.6 Endothermic Materials.

Endotherms are easily quantified using the sample heater and either a fixed temperature scanning mode or a fixed power output from the heater. A test was conducted on a sample of ammonium nitrate in order to demonstrate that the method could be used both for solid materials and for a sample exhibiting endothermic behavior. Ammonium nitrate exhibits four separate endotherms between ambient temperature and about 170° C. Above about 170° C. ammonium nitrate decomposes violently. The test was terminated before this event because of the relatively large size of the sample.

Figure 10:
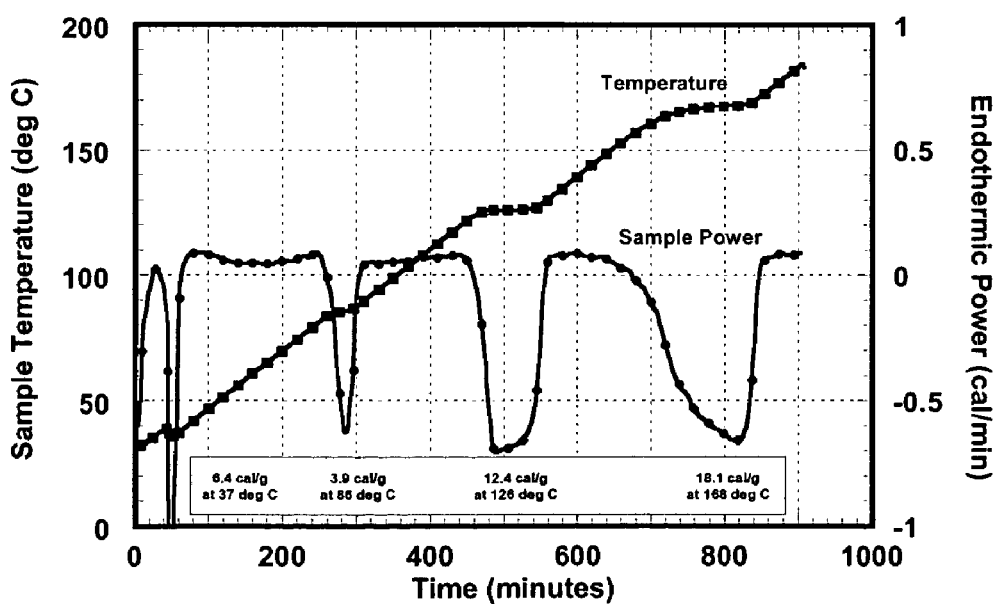
FIG. 10 shows the detection of multiple endotherms in a material.
Figure 11:
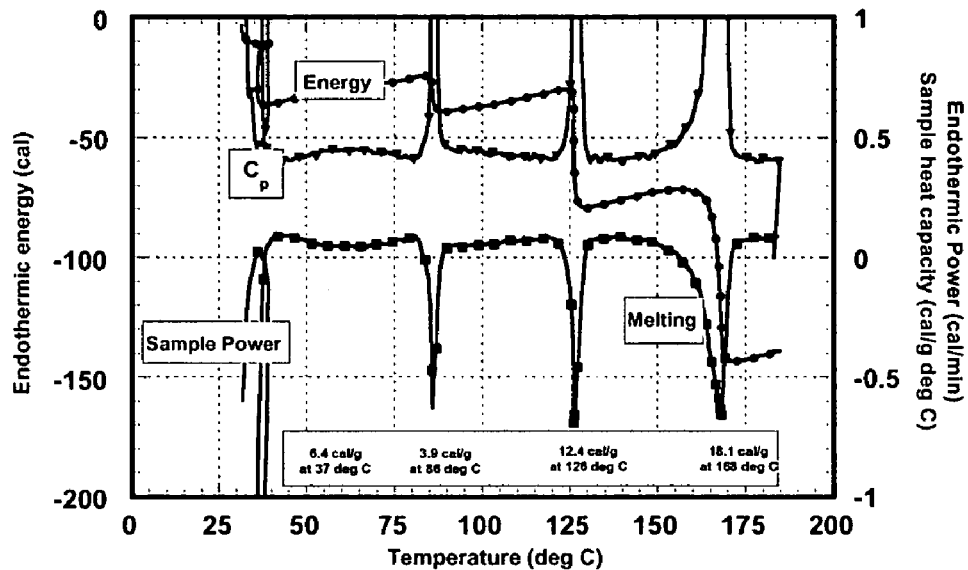
FIGS. 11 and 12 show multiple exotherms and endotherms in scans of, respectively, ammonium nitrate and hydrogen peroxide.

Four grams of ammonium nitrate was heated in a 10.6 gram stainless steel bomb and heated using a constant power output of 50 mW from the sample heater. The chosen power level was sufficient to heat the sample at about 0.2° C./min. Because the sample was a solid, particulate material, this rather small rate was used in order to ensure reasonable heat transfer rates from the heater to the sample while maintaining essentially isothermal conditions throughout the sample and the bomb. FIG. 10 shows the sample temperature and the sample power as a function of time. The figure clearly shows four endotherms, at 37° C., 86° C., 126° C. and fusion of the solid starting at about 150° C. FIG. 11 shows the sample power and energy as a function of the sample temperature and also the apparent sample heat capacity as a function of temperature. During the endothermic events, however, the sample heat capacity is indeterminate. The heat capacity was determined from the heater power output and the known mass and heat capacity of the stainless steel bomb, as described above. The heat of fusion was estimated at 18.1 cal/g at 168° C., which is in good agreement with the published value [10].

2.7 Heat of Decomposition

In all the tests run on DTBP using the bomb compensation method, the estimated heat of decomposition was between about 340 and 360 cal/g of DTBP. Tou and Whiting [2] report values ranging from about 230 to 335 cal/g depending on the mass and type of bomb used in the experiment. Leung, Fauske and Fisher [5] report a value of 290 cal/g measured in the VSP apparatus while Ming-Huei Yue [8] reports an average value of 331 cal/g in the EAC apparatus. An average value of 335 cal/g from round robin testing is reported in [11]. The value found in this work therefore, appears to be high by 7–8%. Some of the variability may be ascribed to inexact knowledge of the heat capacity of the reactants and products over the temperature range of the reaction. However, it was also found in this work that the steel fittings to which the sample bombs are attached in the ARC are cooler than the sample under dynamic conditions. The size of the temperature difference varies with the rate of temperature rise, as described in section 2.2.1. Therefore, under normal operating conditions, a sample undergoing exothermic activity in the standard ARC would be expected to lose some heat at varying rates throughout the course of the exotherm. The loss would not be obvious because at the beginning and end of the exotherm, when the rate of temperature rise is essentially zero, the 'drift' rate in a well calibrated machine will be zero. The varying heat loss rate will also have an effect on the kinetic parameters calculated from the measured self-heat rate data.

In order to check the results and to give additional confidence in the value of the heat of decomposition for DTBP, a test was run on the decomposition of hydrogen peroxide. The decomposition of this material is affected by the state of the reaction bomb wall so obtaining good kinetics in closed, metal vessels is difficult. However, the final state is not affected and since the products of the decomposition are known and completion of reaction can be checked by pressure measurement, the heat of decomposition may be readily obtained from knowledge of the heats of formation of the reactant and products. Thus

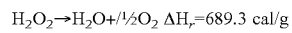

$$H_2O_2 \rightarrow H_2O + \tfrac{1}{2}O_2 \quad \Delta H_r = 689.3 \text{ cal/g}$$

Figure 12:
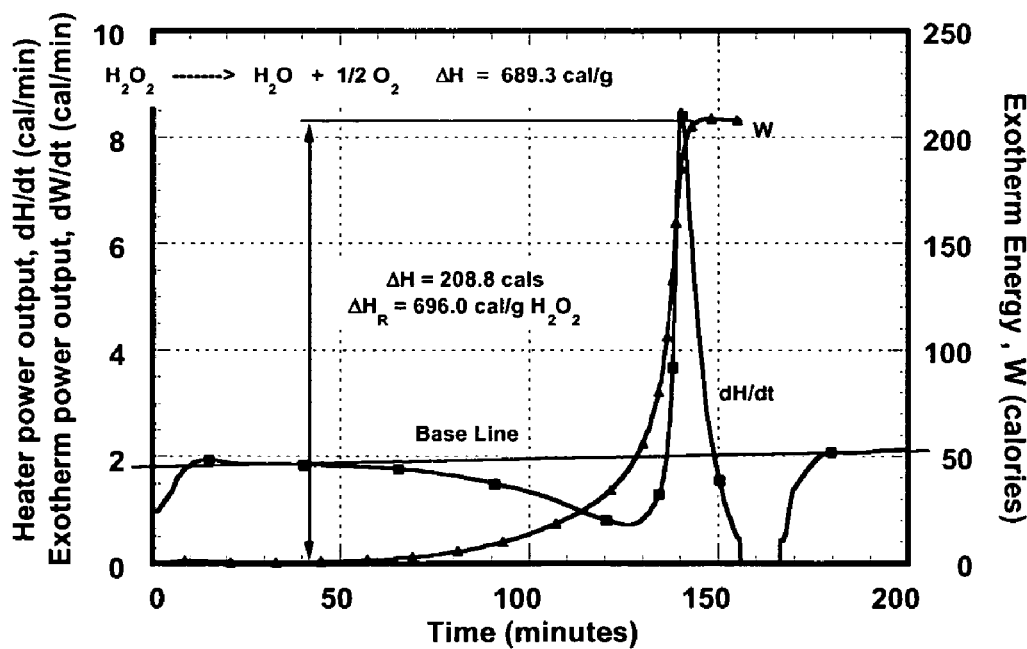

Three grams of a 10% solution of H2O2 was used in a 9.7 gram stainless steel tubular reactor with a small magnetic stir bar weighing 0.23 grams. The sample and bomb were heated at 0.5 C/min. FIG. 12 shows the heater power as a function of time. The base line power output, shown in the figure, enabled the sample power output as a function of time to be calculated using equation [10]. The integration of the sample power output curve, which is also shown in FIG. 12, gave the heat of decomposition of the hydrogen peroxide as 696 cal/g. This figure is within 1% of the expected heat of decomposition of hydrogen peroxide.

2.8 Limit to Compensation of Bomb Thermal Mass

Figure 13:
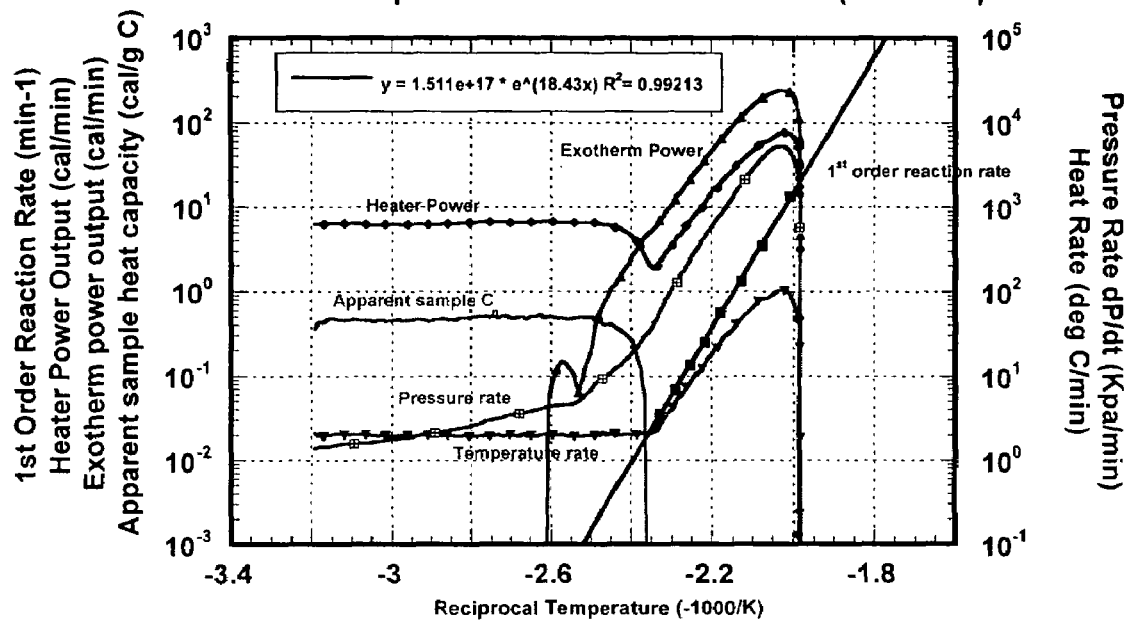
FIG. 13 shows compensation at a $\Phi$ of other than 1.0.

The ability to compensate for the thermal mass of the reaction vessel using a sample heater depends on a number of factors. The principal limitations are the ability to transfer energy from the heater to the sample and the uniform distribution of that heat to the sample bomb. Stirring of the sample is a necessity if heat rates exceed more than a few tens of degrees per minute. If energy rates are very high, the sample heater surface temperature may also exceed the temperature of the sample by a considerable amount, perhaps leading to elevated reaction rates at the surface of the heater. Sample temperature rates as high as 150 ° C./min have been observed in this work. The maximum power available from the sample heater was about 80 cal/min, thus limiting the mass of the bomb that could be successfully compensated. A standard 10 ml, lightweight (~6.0 g) titanium ARC bomb, for instance, could be fully compensated up to a maximum sample heating rate of approximately 100° C./min. On the other hand, a much smaller, stainless steel bomb weighing only 2.5 g could be fully compensated up to about 260° C./min. FIG. 13 shows the result of a test with a 16.7% solution of DTBP in a 10.6 g stainless steel bomb, ramped at 2.0° C./min and compensated for 60% of its mass. It may be seen that the heating rate exceeded 100° C./min and the peak heater power reached its maximum output of about 80 cal/min. Also shown is the apparent sample specific heat as a function of temperature up to the point where exothermic activity occurs. The activation energy for this test was found to be 36.62 Kcal/mol.

3. Scanning Adiabatic Tests at Constant Heat Rate.

An alternative method for running an adiabatic test arises from the methodology described above. If the sample bomb is of very large mass relative to the sample, then the bomb may have sufficient heat capacity to absorb all the heat of reaction during a temperature scan without the temperature rate of the bomb exceeding that of the scan rate. In this case the sample heater is used to control the heating rate of the system (consisting of the sample plus the bomb) at the scan rate throughout the exothermic or endothermic excursion. A limitation arises concerning the thermal conductivity of the material of the sample bomb. If the conductivity is small and the bomb wall thickness is too great, the heat of reaction may not be dissipated to the bomb at a fast enough rate and the sample and bomb can no longer be considered to be in thermal equilibrium.

3.1 Discussion

In a traditional ARC type of experiment, the sample temperature rate continuously increases as the exotherm proceeds. Since the self-heating rate is proportional to the reaction rate the kinetics can be derived from the measured temperature rates. Using equations [10], [11] and [16] a different method of running an adiabatic test is now possible. The heating rate for the system, consisting of the sample and the sample bomb, is controlled at a constant rate by adjusting the power output of the sample heater. As the exotherm accelerates in rate the heater output is decreased in order to keep the rate of heating of the system constant. Therefore, the rate of change of the heater output becomes effectively the new measure of the rate of reaction, and not the rate of change of temperature as in the ARC. The temperature rate in this method is constant and therefore no kinetic information can be extracted using the temperature rate. For this type of test, the sample bomb should be heavy enough to absorb the heat of reaction without increasing the constant rate of temperature rise. Several advantages arise from this mode of testing, including:

- The power requirements for the guard heaters are significantly smaller since they are only required to track the temperature at the given scan rate which would be of the order of a few degrees per minute. The guard heaters in a traditional ARC on the other hand are required to track self-heat rates to about 15° C./min and in the APTAC, where Φ factors are close to 1.0, the heaters can track sample heating rates up to about 400° C./min.
- The massive sample bomb requirement is advantageous from the point of view of pressure. High-pressure requirements can now be very easily met, especially if the scanning temperature rate is kept relatively small.
- The method is less sensitive to small inaccuracies in the calibration of the control and sample thermocouples.
- The test is completed in a considerably shorter time period than the ARC.
- The method also gives the ability to run the test in a differential mode since both a reference sample and the test sample can be heated at the same rate in the same adiabatic environment. Substantial improvements in sensitivity are achieved by running in the differential mode. This method is different from the standard DSC method in that the sample and bomb are heated from the inside of the vessel as opposed to through the wall heating. In addition the sample bomb and the reference bomb are adiabatic, the sample pressure is easily measured and stirring of the sample throughout the test is possible. The differential mode itself offers a number of advantages, chief of which is the ability to 'zero out' the heat capacity of the sample bomb and to negate the effect of small heat losses in the system.

Figure 14:
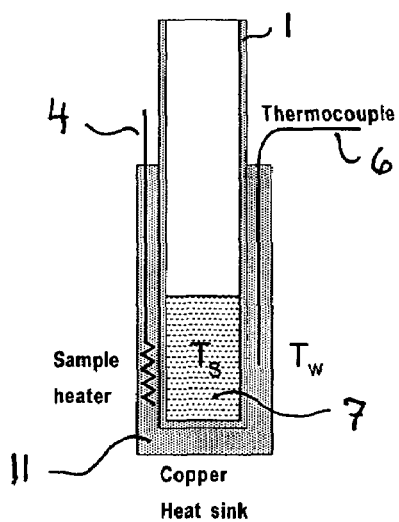
FIG. 14 shows a modified bomb with a heat sink providing extra mass for use with highly exothermic samples.

A heavy walled bomb has the disadvantage that heat conduction from the interior to the outside wall will be slow, especially since sample bombs would normally be constructed of stainless steel or a similar alloy where the thermal conductivity is small. Higher conductivity materials are generally unsuitable because of their lack of strength at higher temperatures, their expense (in the case of precious metals) or their chemical reactivity. In order to overcome these disadvantages, a thinner walled bomb in a material such as stainless steel may be used along with a sleeve of high conductivity material such as copper, as illustrated in FIG. 14. In this case the copper may be, but not necessarily heated from the outside by the 'sample' heater but the operation of the apparatus is in all other aspects the same as that described. The advantages of this type of sample bomb are that higher temperature scanning rates may be used without compromising the thermal conductivity, a sample heater is not required to be inserted into the sample vessel and the sample vessel is less expensive and disposable.

3.2 The Φ Factor for Constant Temperature Scans Tests.

The Φ factor for a test of this type does not have a meaning since the energy absorbed by the bomb has two sources, the sample heat of reaction and the varying output from the heater. The effective thermal mass of the bomb relative to the sample therefore changes as the output of the sample heater changes. Since the heat capacity of the sample bomb is known and the power output from the heater is known, the variation of the Φ factor with sample temperature can be calculated if desired.

3.3 Experimental

Figure 15:
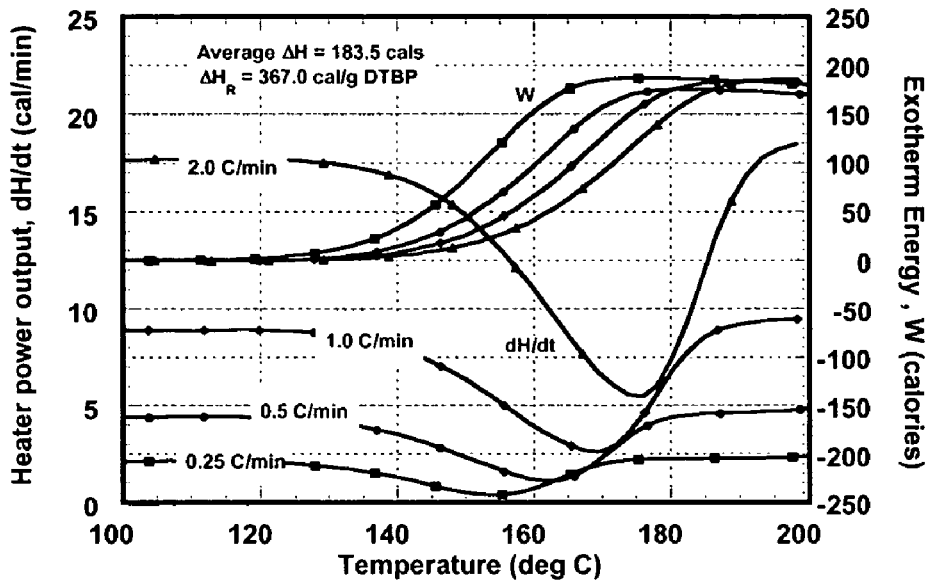
FIGS. 15 and 16 show measurements of the exotherm of DTBP with the heat sink of FIG. 14, at various heating rates.

A number of tests were run using the configuration shown in FIG. 14 and also the configuration shown in FIG. 3 with a heavy-walled Hasteloy C bomb which weighed approximately 71 grams. A 16.7% solution of DTBP in toluene was heated at a number of different rates in the heavy, Hasteloy C bomb. The temperature rate was controlled at a constant rate by adjusting the heater power. The data were analyzed using equation [11] to obtain the heat of reaction and equation [16] to obtain the activation energy and pre-exponential factor from each test. FIG. 15 shows the heater power output and the accumulated exotherm energy output as a function of the sample temperature. Results of the group of tests are summarized in Table 2. The average heat of reaction was found to be 379.0 cals/g of DTBP, which is about 6.0% higher than the value found by the bomb compensation method, as described in section 2. Note that this method does not require knowledge of the sample heat capacity or the bomb heat capacity in order to obtain the heat of reaction. The value of the factor, λ, in equation [3] is set to zero and no compensation for the thermal mass of the bomb occurs.

Figure 16:
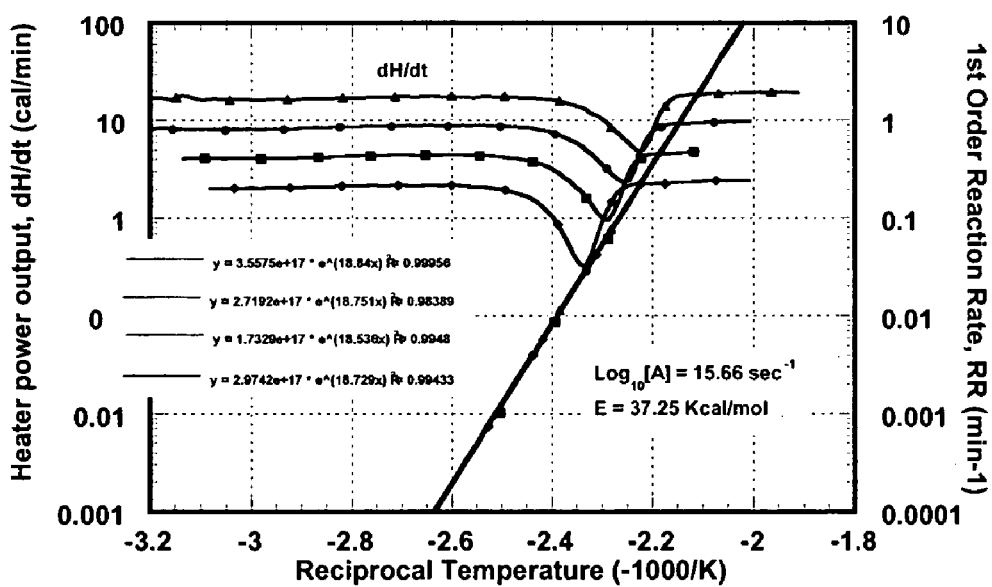

FIG. 16 shows the heater power and the first order reaction rate constant as a function of the reciprocal of the sample temperature for each of the four tests which are shown in the plot. The first order rate constant was calculated using equation [16] and the slopes of the lines gave the activation energy and the pre-exponential factor. The average activation energy for the four tests was 37.20 Kcal/mol, which is about 1.2% greater than the average value found for the bomb compensation method (see Table 1).

Figure 17:
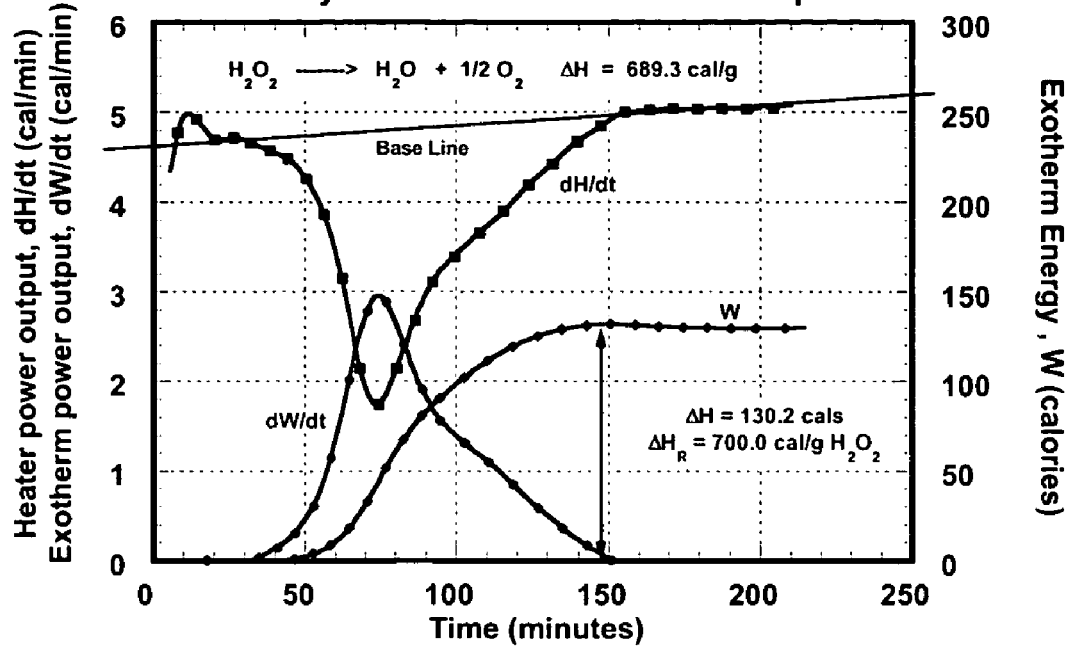
FIGS. 17 and 18 show exotherm measurements with hydrogen peroxide, and demonstrate pressure measurement.

A test was also run on a 3 gram sample of 6.2% hydrogen peroxide solution in a heavy, Hasteloy C reaction vessel. FIG. 17 shows the heater power output, the sample power output and the sample energy output as a function of time. The measured heat of decomposition was found to be 700 cal/g $H_2O_2$, which is about 1.5% greater than the

TABLE 2

Summary of tests with DTBP solution in heavy bomb and at constant scan rate

Figure 18:
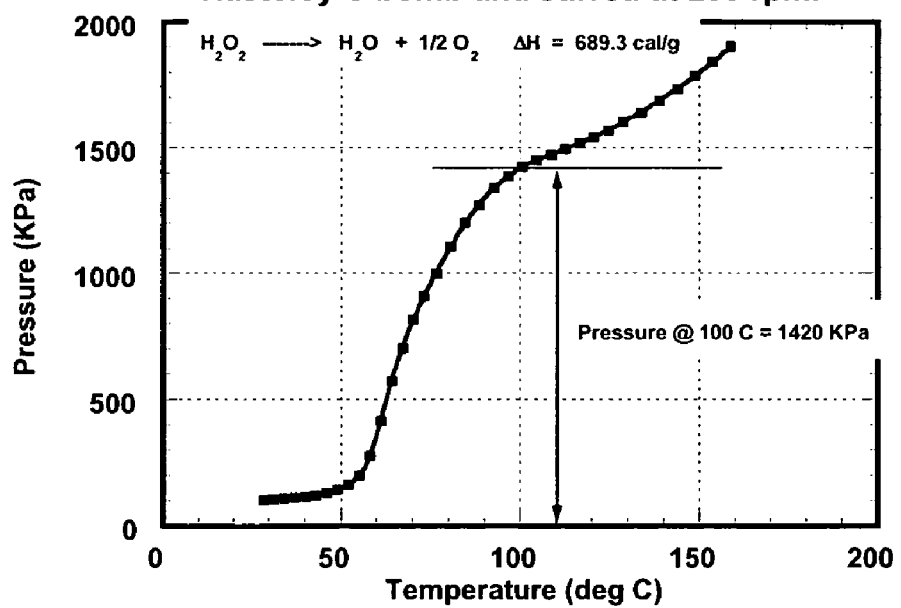

| Conc. (%) | Sample Mass (g) | Bomb Type | Bomb Mass (g) | Scan Rate (C/min) | λ | ΔH$_r$ (Cal/g) | E$_a$ (Kcal/mol) | Log$_{10}$[A] (sec$^{-1}$) |
|---|---|---|---|---|---|---|---|---|
| 16.7 | 3.0 | HC | 71 | 0.25 | 0.0 | 384 | 37.44 | 15.77 |
| 16.7 | 3.0 | HC | 71 | 0.5  | 0.0 | 372 | 37.26 | 15.66 |
| 16.7 | 3.0 | HC | 71 | 1.0  | 0.0 | 380 | 36.84 | 15.46 |
| 16.7 | 3.0 | HC | 71 | 2.0  | 0.0 | 374 | 37.21 | 15.70 |
| 25.0 | 2.0 | HC | 71 | 0.25 | 0.0 | 385 | 37.24 | 15.76 |
|      |     |    |    | AVERAGE |  | 379 | 37.20 | 15.67 | theoretical value of 689.3 cal/g. The measured value was confirmed by analysis of the pressure generated by the decomposition of the hydrogen peroxide to form oxygen and water. FIG. 18 shows the pressure in the reaction bomb as a function of the sample temperature. At 100° C., the pressure was 1420 KPa. Assuming that the oxygen was insoluble in the water at that temperature and that the head space in the reaction vessel was 6.42 mls, this agreed reasonably well with the calculated pressure of 1438.9 KPa, thus confirming the full decomposition of the hydrogen peroxide sample.

A number of additional features can optionally be provided in the improved calorimeter. These include means for starting the calorimetry scan at temperatures below ambient temperature. Any conventional cooling means can potentially be used to equilibrate the sample, the bomb and the associated equipment at a selected sub-ambient temperature. Then the sample run is conducted essentially as described for a scan at ambient or higher temperatures. Cooling means can be, among others, a conventional refrigeration or freezing unit, a device for passing chilled gas through the apparatus, for example from liquid nitrogen or other liquefied or solidified gas (for example, carbon dioxide, argon, helium, or other convenient gas), or simply operating the unit in a chilled environment (walk in refrigerator or freezer). Attention will be paid to preventing condensation of water on the apparatus, perhaps requiring shrouding in a dry gas atmosphere. Any temperature is in principle available. As a practical matter, starting temperatures at or above the boiling point of liquid nitrogen, ca. 190 degrees K, are preferred, and most chemistry will occur at higher temperatures.

Another option is stirring of the sample, which is particularly useful with samples which are liquid, or in some cases present as fine and preferably non-aggregating powders. A magnetic stirrer, with a stirring magnet inside the bomb and a drive magnet outside, has been used in commercial apparatuses. A mechanical stirrer would also be possible, although access through the neck of the bomb is restricting.

Another option is measurement of the pressure produced by the sample during thermal analysis. This is currently done in some commercial calorimeters. The bomb can be sealed, for example periodically during the run, or for all of a run over a narrow temperature range, and the pressure inside the bomb is measured by a pressure transducer or other sensor. An alternative, which allows sealing of the bomb over a wide pressure range, is to place the bomb and the enclosure inside a pressurizable container, and then applying external pressure to balance the pressure found inside the bomb. Such a procedure is currently used, and could be used in the calorimeter of the invention, to allow the use of thin-walled bombs, which would absorb less heat from the sample.

The sample size is not a critical aspect of the invention. When the sample is not limited in amount, and does not have a strong exotherm or decomposition, the range of 1 to 5 grams is convenient. There is seldom a need for larger samples, unless a very subtle exotherm or endotherm is to be measured accurately. Smaller samples may be used, depending on the sensitivity and precision required, which may be as small as 100 mg. The sample volume in the bomb will be adjusted accordingly. A typical bomb volume will be in the range of about 1 cc to 20 cc, but may be made larger or smaller as required to accommodate a sample.

Likewise, a wide range of heating rates is possible. An upper rate could be in the range of 1500 calories/minute, or about 100 W, but lower rates can be used down to the limits of sensitivity and stability. These can be as low as about 0.0001 calorie per minute, or about 5 to 7 microwatts. The ability to measure over such a wide range of heating rates is an advantage of the present invention, that is not found in other systems.

Any method of measurement of temperatures can be used. The preferred method is the use of a thermocouple, typically a type N thermocouple. Thermistors can be used, especially below about 100 deg. C.

The invention had been described in terms of having the sample heater inside of the bomb, as illustrated in FIG. 3. In many instances this is the preferred mode. However, in other cases the sample heater side can be inside the wall of the bomb, or inside the wall of a heat sink or high-heat-conductivity material that is in thermal contact with the bomb, and still provide all of the benefits of the invention. Moreover, although not illustrated, and less preferred, the sample heater can be mounted on the outside of the bomb. This will provide similar results when the rate of heating can be constant, particularly with a well calibrated bomb, but is much harder to use to track an exotherm, especially a "runaway" exotherm.

CONCLUSIONS

An improved method has been developed for obtaining adiabatic calorimetry data using a sample heater to quantify thermal events. The method uses a sample size of the order 1–5 gram so that pressure is also routinely measured. The effect of the mass of the reaction vessel on the results can be negated by dynamic thermal compensation, such that the effective Φ factor for the test can be 1.0. Heat effects from the sample, including endothermic events, are quantified without reference to the specific heat of the sample. The sample and reaction vessel can be heated at a constant temperature rate and thus dramatically reduce testing time over that for conventional adiabatic calorimetry using the Heat-Wait-Search strategy. Sample specific heats can be measured prior to any thermal event. The exotherm detection sensitivity is at least as good as existing adiabatic calorimeters employing the HWS strategy, although the detection sensitivity is dependent on the temperature scanning rate.

The invention has been described in particular embodiments and examples, which are provided to teach how to make and use the invention. Many variations and equivalents will be apparent to the skilled person, and the invention is not to be limited to the scope of the description and examples, but by the scope of the claims.

REFERENCES

1. Townsend, D. I, and Tou, J. C., Thermal Hazard Evaluation by an Accelerating Rate Calorimeter, Thermochimica Acta, 37 (1980) 1–30.
2. Tou, J. C, and Whiting, L. F., The Thermokinetic Performance of an Accelerating Rate Calorimeter, Thermochimica Acta, 48 (1981) 21–42.
3. Ahmed, M., and Fisher, H. G., and Janeshek, A. M.; Reaction Kinetics from Self-Heat Data-Data Correction for the Depletion of Sample. International Symposium on Runaway Reactions, AIChE, 1989, 331–341.
4. Bench Scale ERS Sizing Tools: Equipment Details, Test Procedures and Illustrations, Fauske and Associates, Inc., Report No. FAI/84-4, revised, 1984.
5. Leung, J. C., and Fauske, H. K., and Fisher, H.G., Thermal Runaway Reactions in a Low Thermal Inertia Apparatus, Thermochimica Acta, 104 (1986) 13–29.
6. Young, M. A., and Chippett, S., Design and Operation of an Automatic Pressure Tracking Adiabatic Calorimeter (APTAC), International Symposium on Runaway Reactions and Pressure Relief Design, AIChE, 1995, 23–57.
7. Singh, J., Phi-Tec: Enhanced Vent Sizing Calorimeter-Applications and Comparison with Existing Devices, International Symposium on Runaway Reactions, AIChE, 1989, 313–330.
8. Yue, M-H.; An Enhanced Adiabatic Calorimeter for Thermal Hazard Analysis. Journal of Hazardous Materials, 38, 1994, 13–25.
9. Chippett, S., Ralbovsky, P., Granville, R; The APTAC: A high Pressure, Low Thermal Inertia, Adiabatic Calorimeter. International Symposium on Runaway Reactions, Pressure Relief Design and Effluent Handling. AIChE, 1998, 81–108.
10. Dean, J. A., Editor, Lange's Handbook of Chemistry. 11th Edition. McGraw-Hill. 1973.
11. Leung, J., Creed, M. and Fisher, H.G., Round Robin Vent Sizing Package Results. International Symposium on Runaway Reactions, AIChE, 1989, 264–280.

Patents describing calorimeters include U.S. Pat. Nos. 3,593,577; 4,208,907; 4,439,048; 4,892,707; 4,963,499; 5,547,282; 5,806,979; 6,157,009 and 6,513,969; WO 99/60356; EP 0 286 580; and the abstract of Japanese application 53049395.

The invention claimed is:

1. A method, for use in an adiabatic scanning calorimeter, for removing the influence of the mass of a bomb from the measurement of the thermal properties of a sample undergoing an exothermic or endothermic reaction, comprising the steps of:
    a) placing a sample in a bomb;
    b) initially heating the sample at a predetermined rate of temperature increase, by adjusting the power output of a sample heater;
    c) calculating the rate of heat loss to the bomb from the sample;
    d) adjusting the sample heater power output to equal the heat loss rate to the sample bomb;
    e) adjusting the power input to one or more guard heaters to prevent the loss of heat from the exterior surface of the bomb; and
    f) calculating the amount of heat absorbed or evolved from the sample to change the sample temperature by a defined amount, by subtracting the heat supplied by the sample heater from the change in the sensible heat of the sample and the sample bomb.

2. The use of the method of claim 1 to calculate the heat capacity of a sample, in a temperature range in which there are no sample exotherms or endotherms, comprising the additional steps of
    (g) establishing the heat capacity of said bomb
    (h) calculating the amount of energy used by the sample heater to raise the temperature of the bomb;
    (i) subtracting the energy used to heat the bomb from the total energy supplied to find the heat energy absorbed by the sample, and
    (j) dividing the heat absorbed by the sample by the sample mass to obtain the heat capacity of a sample.

3. The use of the method of claim 1 for determining the amount of energy absorbed by a sample during an endotherm, the method comprising the additional steps of:
    (g) selecting a predetermined rate of temperature rise that is sufficiently slow to maintain essentially isothermal conditions within the bomb;
    (h) increasing power to the sample heater as required to maintain the predetermined rate of temperature rise; and
    (i) calculating the amount of energy absorbed by a sample during the endotherm as the integral of the increase in the sample heater power output above the power applied by the sample heater prior to the start of the endotherm.

4. The use of the method of claim 1 to determine the sample energy release rate or absorption rate by subtracting the sample heater power output from the sum of the rates of change of the sensible energies of the sample and the sample bomb, by the use of the equation $$dW/dt = (M_s C_s + M_b C_b)(dT_w/dt) - P$$

or an equation functionally equivalent thereto, where (dW/dt) is the sample energy release rate, P is the sample heater power and $(M_s C_s + M_b C_b)(dT_w/dt)$ is the rate of change of the sensible energy of the sample and the sample bomb, wherein the rate of change of the sensible energy of the sample and the sample bomb are obtained from the method of claim 1 together with the measured rate of temperature rise of the sample and the sample bomb.

5. The use of the method of claim 4 to calculate the total energy released or absorbed by the sample during an exotherm or endotherm, the method comprising the additional step of integrating the equation in method 17 between the temperature limits at the beginning of the reaction and the end of the reaction.

6. A method, for use in an adiabatic scanning calorimeter, for determining the heat capacity of a sample at a temperature in a certain range, the range characterized in the absence of exotherms and endotherms, the method comprising the steps of:
  a) establishing the heat capacity of a bomb
  b) placing the sample in the bomb;
  c) heating the sample at a constant rate using a sample heater;
  d) preventing heat loss from the bomb using one or more guard heaters;
  e) calculating the amount of energy used by the sample heater to raise the temperature of the bomb;
  f) subtracting the energy used to heat the bomb from the total energy supplied to find the heat energy absorbed by the sample, and
  g) dividing the heat absorbed by the sample by the sample mass to obtain the heat capacity.

7. A method, for use in an adiabatic scanning calorimeter, for determining the amount of energy absorbed by a sample during an endotherm, the method comprising the steps of:
  a) placing a sample in a sample bomb, the sample bomb having a known mass and heat capacity;
  b) heating the sample using a sample heater at a constant rate of applied power, the rate being selected to be sufficiently slow to maintain essentially isothermal conditions within the bomb;
  c) preventing heat loss from the external surface of the bomb using one or more guard heaters;
  d) calculating the amount of energy absorbed by the sample during the endotherm from the measured change in the rate of temperature decrease of the sample and bomb and the known heat capacity and mass of the sample bomb and the known power applied to the sample by the sample heater.

8. A method, for use in an adiabatic scanning calorimeter, for determining the amount of energy released or absorbed by a sample during an exothermic or endothermic reaction, the method comprising the steps of:
  a) placing a sample in a sample bomb;
  b) heating the sample using a sample heater at a constant rate of temperature increase, the rate being selected to be sufficiently slow to maintain essentially isothermal conditions within the bomb;
  c) preventing heat loss from the external surface of the bomb using one or more guard heaters;
  d) decreasing or increasing the power to the sample heater as required to maintain the pre-selected rate of temperature rise; and
  e) calculating the amount of energy released or absorbed by the sample during the reaction from the difference between the power required to maintain the selected rate of temperature rise, and the power that would have been required to maintain said rate of temperature rise of the sample and the sample bomb if no reaction had occurred in the sample.

9. A method, for use in an adiabatic scanning calorimeter having two or more sample bombs, for determining the amount of energy released or absorbed by multiple samples during a chemical or physical change, the method comprising the steps of:
  a) placing the samples in the sample bombs;
  b) heating the samples using sample heaters at a constant rate of temperature increase, the rate being pre-selected to be sufficiently slow to maintain essentially isothermal conditions within the bombs;
  c) preventing heat loss from the external surfaces of the bombs using one or more guard heaters;
  d) decreasing or increasing the power to the sample heaters as required to maintain the pre-selected rate of temperature rise within the samples; and
  e) calculating the amount of energy released or absorbed by the samples during the reactions from the difference between the power required to maintain the selected rate of temperature rise, and the power that would have been required to maintain said rate of temperature rise of the samples and the sample bombs if no reaction had occurred in the samples.

10. A method, for use in an adiabatic calorimeter, for determining the energy release or absorption rate of a sample, the method comprising the steps of
  a) placing a sample in a bomb;
  b) heating the sample and the bomb at a constant power input using a sample heater;
  c) preventing heat loss from the bomb and sample using one or more guard heaters;
  d) calculating the sample energy release or absorption rate from the measurement of the rate of temperature change of the system and the constant power output from the heater by the use of the equation $$dW/dt = P_0[\{(dT_w/dt)/(dT_0/dt)\} - 1]$$

or an equation functionally equivalent thereto, where $(dW/dt)$ is the sample energy release (or absorption) rate; $(dT_0/dt)$ is the initial rate of temperature rise of the system due to the constant power input, $P_0$, and $(dT_w/dt)$ is the rate of temperature rise of the sample and the sample bomb.

11. The use of the method of claim 10 to calculate the total energy released or absorbed by the sample during an exothermic or endothermic reaction, the method comprising the additional step of integrating the equation in method 19 between the temperature limits at the beginning of the reaction and the end of the reaction.

* * * * *